(12) United States Patent
Jackman

(10) Patent No.: US 10,426,597 B1
(45) Date of Patent: Oct. 1, 2019

(54) SOFT TISSUE REBALANCING DEVICE AND METHOD

(71) Applicant: Matthew Jackman, Sherman, TX (US)

(72) Inventor: Matthew Jackman, Sherman, TX (US)

( * ) Notice: Subject to any disclaimer, the term of this patent is extended or adjusted under 35 U.S.C. 154(b) by 0 days.

(21) Appl. No.: 16/054,787

(22) Filed: Aug. 3, 2018

(51) Int. Cl.
*A61F 2/08* (2006.01)
*A61F 2/42* (2006.01)

(52) U.S. Cl.
CPC ............. *A61F 2/0811* (2013.01); *A61F 2/08* (2013.01); *A61F 2002/0858* (2013.01); *A61F 2002/0882* (2013.01)

(58) Field of Classification Search
CPC .. A61F 2/08; A61F 2/0805; A61F 2002/0829; A61F 2002/0835; A61F 2002/0858; A61F 2002/0864; A61F 2/42–2002/4271; A61L 2430/10
See application file for complete search history.

(56) References Cited

U.S. PATENT DOCUMENTS

2018/0228596 A1* 8/2018 Wyland ............. A61B 17/0401

* cited by examiner

*Primary Examiner* — Brian A Dukert
(74) *Attorney, Agent, or Firm* — Wilson Daniel Swayze, Jr.

(57) ABSTRACT

A soft tissue rebalancing method to rebalance a phalanx may include the steps of: forming a mesh body portion having a ligament mesh portion and a braided mesh portion; positioning the mesh body portion on a phalanx; connecting the ligament mesh portion to a driver tool; tensioning the ligament mesh portion to increase the tension of the mesh body portion on the phalanx; performing transverse plane correction on the phalanx.

4 Claims, 13 Drawing Sheets

SOFT TISSUE REBALANCING DEVICE AND METHOD

FIELD OF THE INVENTION

The present invention relates to a soft tissue rebalancing device.

BACKGROUND

The metatarsophalangeal joints (MTP joints) are the joints between the metatarsal bones of the foot and the proximal bones (proximal phalanges) of the toes. They are condyloid joints, meaning that an elliptical or rounded surface (of the metatarsal bones) comes close to a shallow cavity (of the proximal phalanges).

The movements permitted in the metatarsophalangeal joints are flexion, extension, abduction, adduction and circumduction Metatarsophalangeal joint pain is a common cause of metatarsalgia. Metatarsophalangeal joint pain most commonly results from misalignment of the joint surfaces with altered foot biomechanics, causing joint subluxations, flexor plate tears, capsular impingement, and joint cartilage destruction (osteoarthrosis). Misaligned joints may cause synovial impingement, with minimal if any heat and swelling (osteoarthritic synovitis).

The phalanges (phalanx) are digital bones in the hands and feet of most vertebrates. In primates, the thumbs and big toes have two phalanges while the other digits have three phalanges. The phalanges are classed as long bones.

The phalanges are the bones that make up the fingers of the hand and the toes of the foot. There are 56 phalanges in the human body, with fourteen on each hand and foot. Three phalanges are present on each finger and toe, with the exception of the thumb and large toe, which possess only two. The middle and far phalanges of the fourth and fifth toes are often fused together (symphalangism). The phalanges of the hand are commonly known as the finger bones. The phalanges of the foot differ from the hand in that they are often shorter and more compressed, especially in the proximal phalanges, those closest to the body.

A phalanx is named according to whether it is are proximal, middle, or distal and its associated finger or toe. The proximal phalanges are those that are closest to the hand or foot. In the hand, the prominent, knobby ends of the phalanges are known as knuckles. The proximal phalanges join with the metacarpals of the hand or metatarsals of the foot at the metacarpophalangeal joint or metatarsophalangeal joint. The intermediate phalanx is not only intermediate in location, but usually also in size. The thumb and large toe do not possess a middle phalanx. The distal phalanges are the bones at the tips of the fingers or toes. The proximal, intermediate, and distal phalanges articulate with one another through interphalangeal articulations.

Head is the distal end of the metatarsal or distal end. It is flattened from side to side. Head of each metatarsal articulates with respective phalanx to form metatarsophalangeal joint. A constriction proximal to head is called anatomical neck.

A Chinese finger trap (also known as a Chinese finger puzzle, Chinese thumb cuff, Chinese handcuffs and similar variants) is a gag toy used to play a practical joke on unsuspecting children and adults. The finger trap is a simple puzzle that traps the victim's fingers (often the index fingers) in both ends of a small cylinder woven from bamboo. The initial reaction of the victim is to pull their fingers outward, but this only tightens the trap. The way to escape the trap is to push the ends toward the middle, which enlarges the openings and frees the fingers.

SUMMARY

A soft tissue rebalancing method to rebalance a phalanx may include the steps of:
  forming a mesh body portion having a ligament mesh portion and a braided mesh portion;
  positioning the mesh body portion on a phalanx;
  connecting the ligament mesh portion to a driver tool;
  tensioning the ligament mesh portion to increase the tension of the mesh body portion on the phalanx;
  performing transverse plane correction on the phalanx.

The method further includes the step of securing the main body portion to a metatarsal neck.

The method further includes the step of the step of forming a hole in the phalanx.

The method further includes the step of securing the ligament mesh portion by a tack positioned in the hole.

BRIEF DESCRIPTION OF THE DRAWINGS

The invention may be understood by reference to the following description taken in conjunction with the accompanying drawings, in which, like reference numerals identify like elements, and in which.

DETAILED DESCRIPTION

Figure 1:
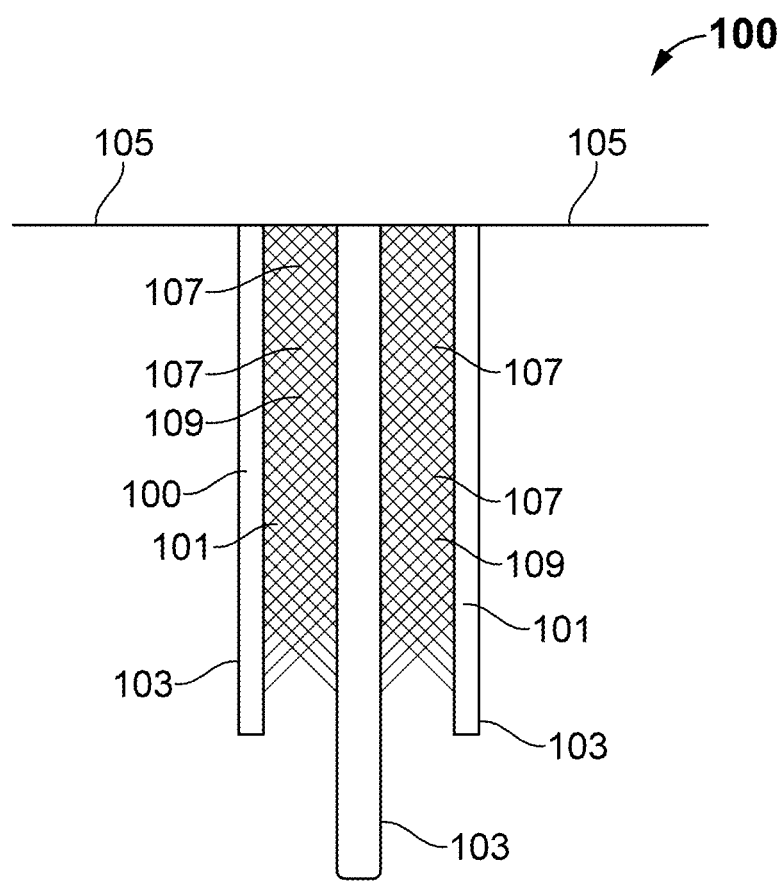
FIG. 1 illustrates a side view of the soft tissue rebalancing device of the present invention.

FIG. 1 illustrates the soft tissue rebalancing device 100 of the present invention and the soft tissue rebalancing device 100 may include a mesh body portion 101, a braided mesh portion 103 to recreate the ligaments and the ligament braided mesh portion 105 simply wraps the proximal phalange base to reconstruct and or repair the phalanx joint, for example the phalanx more particularly the plantar plate. The mesh body portion 101 may include a grid of first filament wire/cords 107 and second filament wire/cords 109 which may be substantially perpendicular to the first filament wire/cords 107. The mesh body portion 101 may be formed as a substantial cylinder but may be formed as a oval, rectangle or other shape. The first filament wire/cords 107 may be connected at an acute angle to the braided mesh portion 103, and the second filament wire/cords 109 may be connected at an acute angle to the braided mesh portion 103. The first filament wire/cords 107 and the second filament wire/cords 109 may be rigid or may be flexible. The diameter of the braided mesh portion 103 is reduced when either the braided mesh portion 103 and/or the filament mesh portion 105 is extended from the mesh body portion 101. This allows the mesh body portion 101 to engage the phalanx with a pressure fiction connection with the phalanx.

The braided mesh portion 103 may extend substantially axially, and a first end of the ligament braided mesh portion 105 may be connected to the braided mesh portion 103. Another end of the ligament braided mesh portion 105 may be unconnected or may be connected to the phalanx 111.

Figure 2:
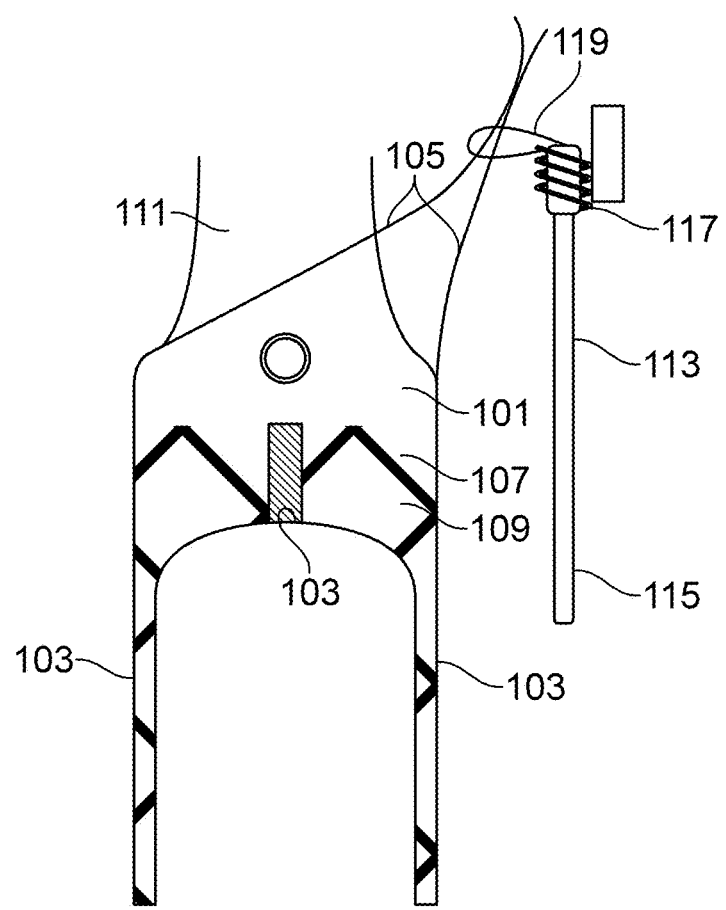
FIG. 2 illustrates a side view of the soft tissue rebalancing device and driver tool of the present invention.

The braided mesh portion 103 may extend along and beyond the axial length of the mesh body portion 101 in order to provide a portion of the braided mesh portion 103 to be attached to the metatarsal. The soft tissue rebalancing device 100 may operate as the Chinese finger trap. The braided mesh portion 103 functions to tether the toe to the metatarsal FIG. 2 illustrates the soft tissue rebalancing device 100 being applied to the phalanx 111. The mesh body portion 101 encloses or encircles the phalanx 111 and a driver tool 113 exerts tension on the ligament mesh portion 105 to decrease the diameter of the mesh body portion 101. The driver tool 113 may include a handle 115 which may be connected to a threaded driver screw 117 or other such device in order to gather up the ligament mesh portion 105 in order to tighten/constrict the mesh body portion 101 around the phalanx 111. The driving tool 113 may include a loop 119 having a central aperture to engage the ligament mesh portion 103.

Figure 3:
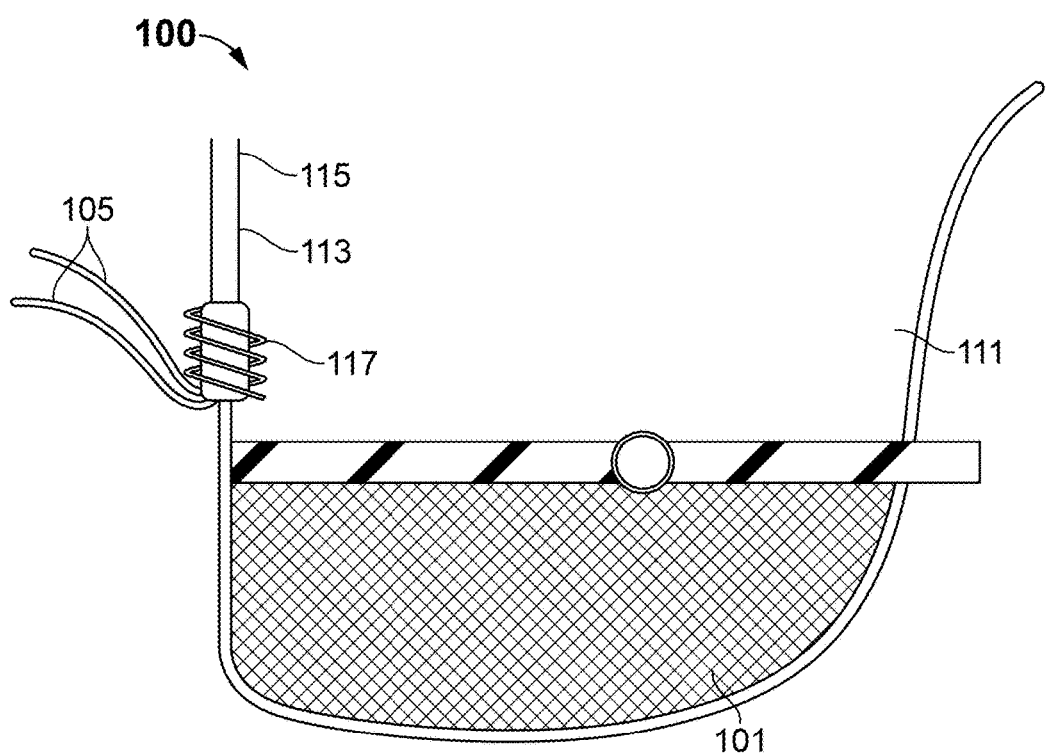
FIG. 3 illustrates a side view of the soft tissue rebalancing device and driver tool of the present invention.

FIG. 3 illustrates a lateral view of the soft tissue rebalancing device 100 being applied to the phalanx 111. The mesh body portion 101 encloses the phalanx 111 and a driver tool 113 exerts tension on the ligament mesh portion 105 to decrease the diameter of the mesh body portion 101. The driver tool 113 may include a handle 115 which may be connected to a threaded driver screw 117 or other such device in order to gather up the ligament mesh portion 105 in order to tighten/constrict the mesh body portion 101 around the phalanx 111. The driving tool 113 may include a loop 119 having a central aperture to engage the ligament mesh portion 103.

Figure 5:
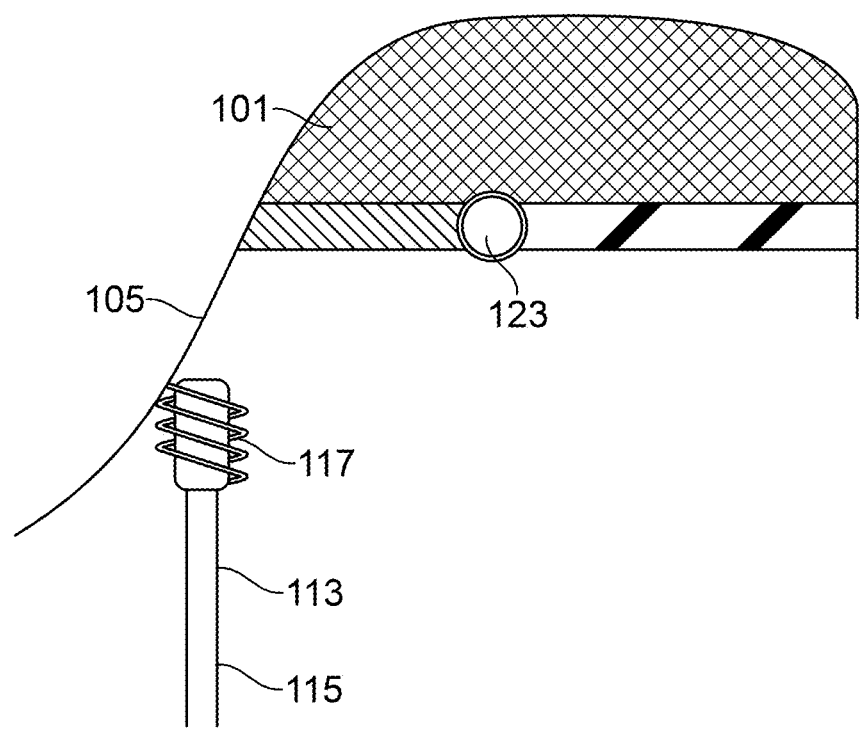
FIG. 5 illustrates a side view of the soft tissue rebalancing device and driver tool of the present invention.

A dorsal to plantar hole is drilled in the proximal phalanx such as aperture 123 as shown in FIG. 5. A dorsal hole and a plantar hole are drilled in the proximal phalanx. Through the dorsal to plantar hole in the proximal phalanx, the loose ends of the braided filament portion 105 are tensioned circumferentially around the base of the proximal phalanx and secured with the set screw. The excess filament portion 105 is cut.

Figure 4:
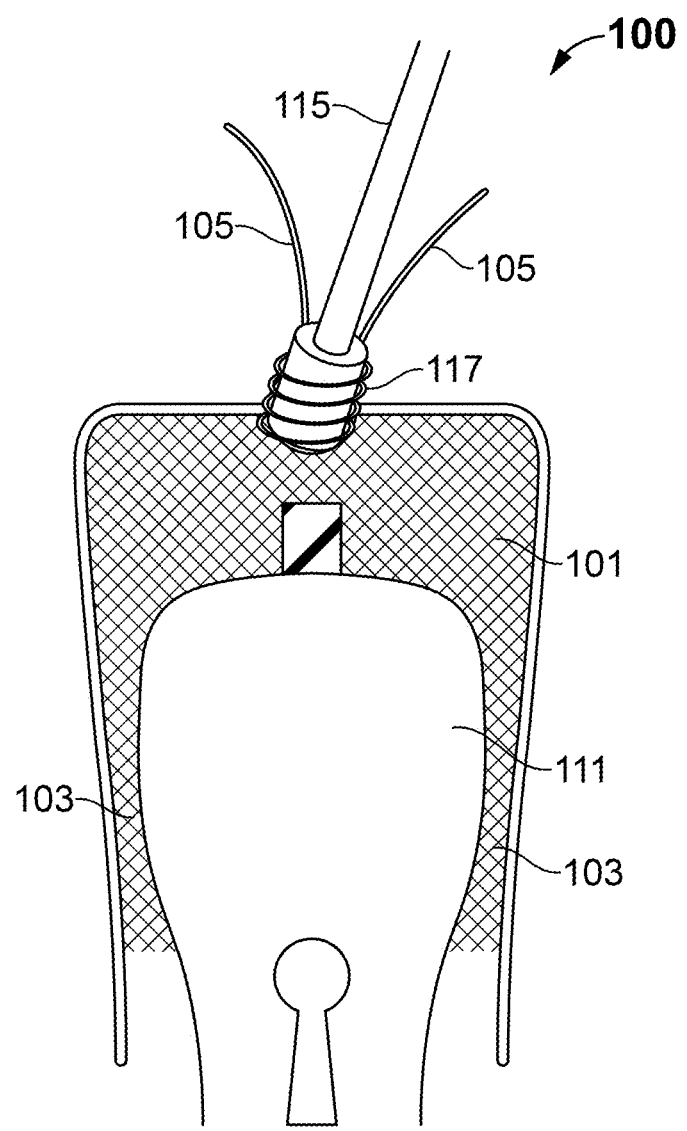
FIG. 4 illustrates a side view of the soft tissue rebalancing device and driver tool of the present invention.

FIG. 4 illustrates a dorsal view of the soft tissue rebalancing device 100 being applied to the phalanx 111. The mesh body portion 101 encloses the phalanx 111 and a driver tool 113 exerts tension on the ligament mesh portion 105 to decrease the diameter of the mesh body portion 101. The driver tool 113 may include a handle 115 which may be connected to a threaded driver screw 117 or other such device in order to gather up the ligament mesh portion 105 in order to tighten/constrict the mesh body portion 101 around the phalanx 111. The driving tool 113 may include a loop 119 having a central aperture to engage the ligament mesh portion 103.

A dorsal to plantar hole are drilled in the proximal phalanx. Through the dorsal to plantar hole in the proximal phalanx, the loose ends of the braided filament 105 are tensioned circumferentially around the base of the proximal phalanx and secured with a set screw 117 (in a trans friction fashion).

FIG. 5 illustrates the mesh body portion 101 positioned on the phalanx 111 and the driving tool 113 including the handle 115 and driving screw 117 to engage the ligament mesh portion 105. FIG. 5 additionally illustrates a aperture 123 to cooperate with a tack 125 (shown in FIG. 6) to secure and hold the ligament mesh portion 105 after the driving tool 113 has placed predetermined tension on the ligament mesh portion 105.

Once the mesh body portion 101 has been tightly secured to the proximal phalanx with a tack, nail, pin or other device, the ligament mesh portion 105 is passed through a hole which has been previously formed in the metatarsal neck from plantar to dorsal. Predetermined tension is placed on the ligament mesh portion 105 and then the ligament mesh portion 105 is secured or from a set screw. At this time, transverse plane correction can be achieved by predetermined tension on the medial and lateral collateral ligament mesh portion 103 and then secures them to the metatarsal neck.

Figure 6:
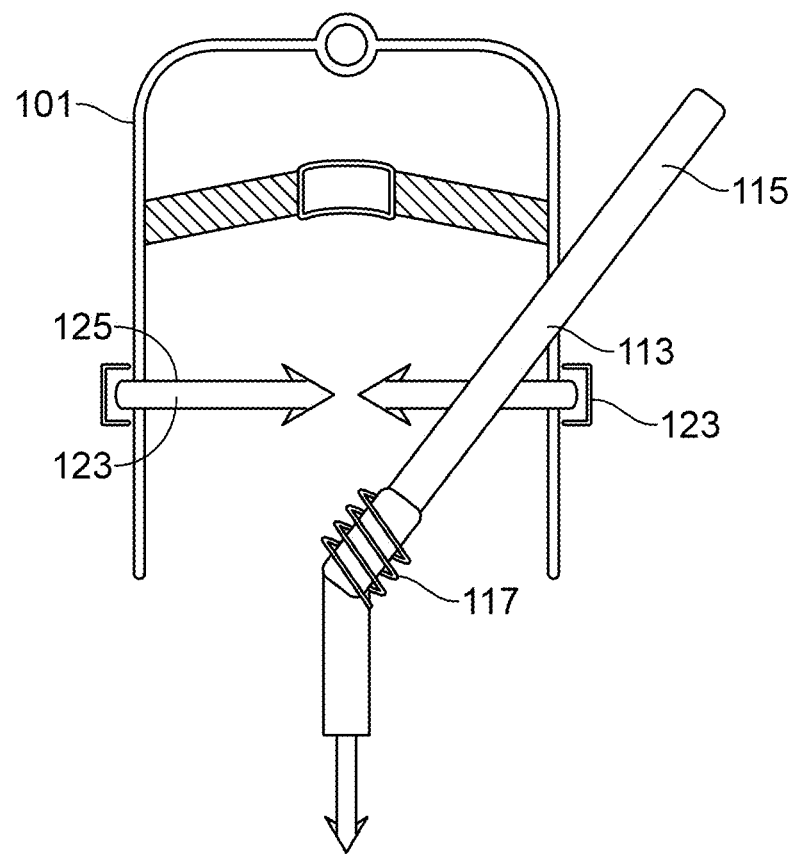
FIG. 6 illustrates a side view of the soft tissue rebalancing device, driver tool, and holding device of the present invention.

FIG. 6 illustrates the mesh body portion 101 positioned on the phalanx 111 and the driving tool 113 including the handle 115 and driving screw 117 to engage the ligament mesh portion 105.

FIG. 6 additionally illustrates a aperture 123 to cooperate with a tack 125 (shown in FIG. 6) to secure the ligament mesh portion 105 after the driving tool 113 has placed predetermined tension on the ligament mesh portion 105.

Figure 7:
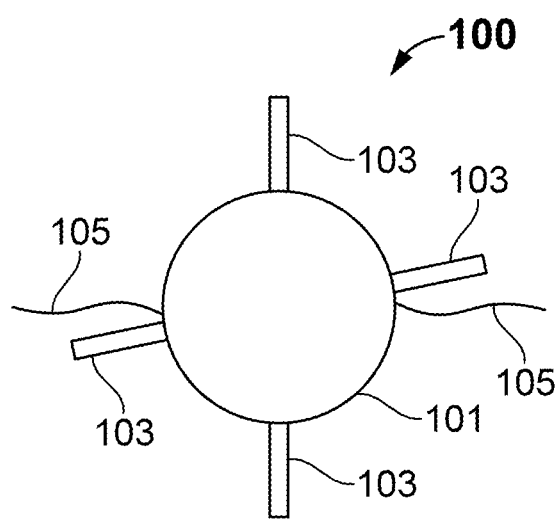
FIG. 7 illustrates a top view of the soft tissue rebalancing device of the present invention.

FIG. 7 illustrates a top view of the soft tissue rebalancing device 100 of the present invention and illustrates the mesh body portion 101, the braided mesh portion 103 and the ligament mesh portion 105.

Figure 8:
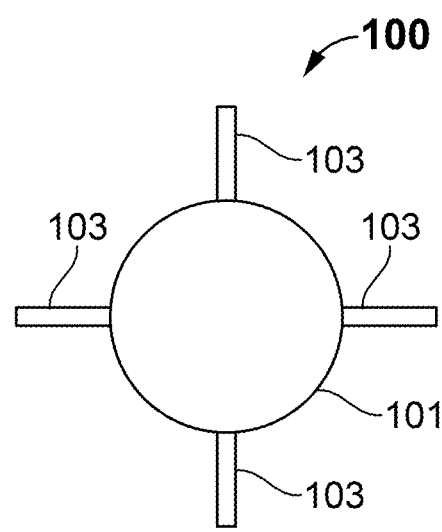
FIG. 8 illustrates a bottom view of the soft tissue rebalancing device of the present invention.

FIG. 8 illustrates a bottom view of the soft tissue rebalancing device 100 of the present invention and illustrates the mesh body portion 101, the braided mesh portion 103 and the ligament mesh portion 105.

Figure 9:
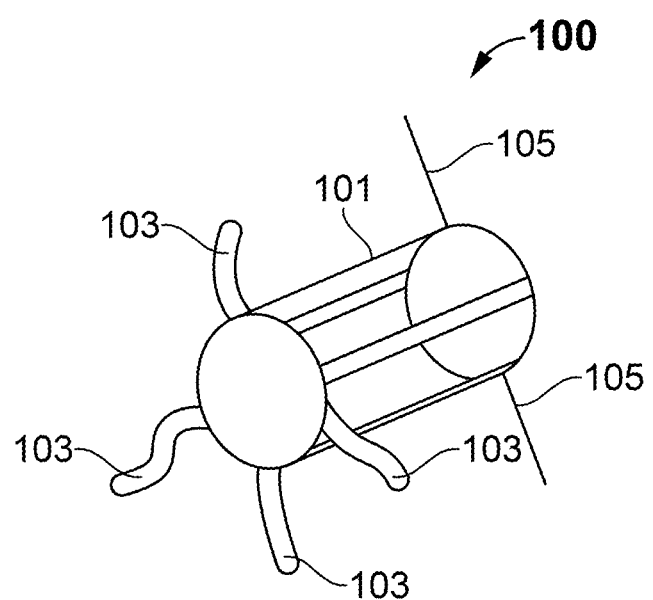
FIG. 9 illustrates a perspective view of the soft tissue rebalancing device of the present invention.

FIG. 9 illustrates a perspective view of the soft tissue rebalancing device 100 of the present invention and illustrates the mesh body portion 101, the braided mesh portion 103 and the ligament mesh portion 105.

FIG. 9 suggests that the mesh encircles the joint circumferentially which it does not. It wraps on either side to about mid-joint level (recreating the lateral collateral ligaments with braided thickening 103).

Figure 10:
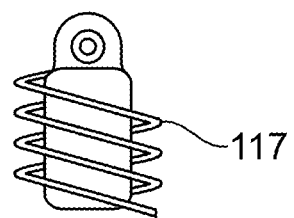
FIG. 10 illustrates a first driving screw of the present invention.

FIG. 10 illustrates a first drive screw 117 of the present invention.

Figure 11:
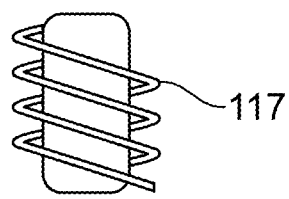
FIG. 11 illustrates a second driving screw of the present invention.

FIG. 11 illustrates a second drive screw 117 of the present invention.

Figure 12:
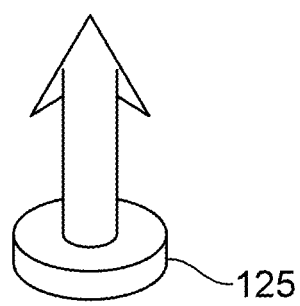
FIG. 12 illustrates a tack of the present invention.

FIG. 12 illustrates a tack 125 of the present invention.

Figure 13:
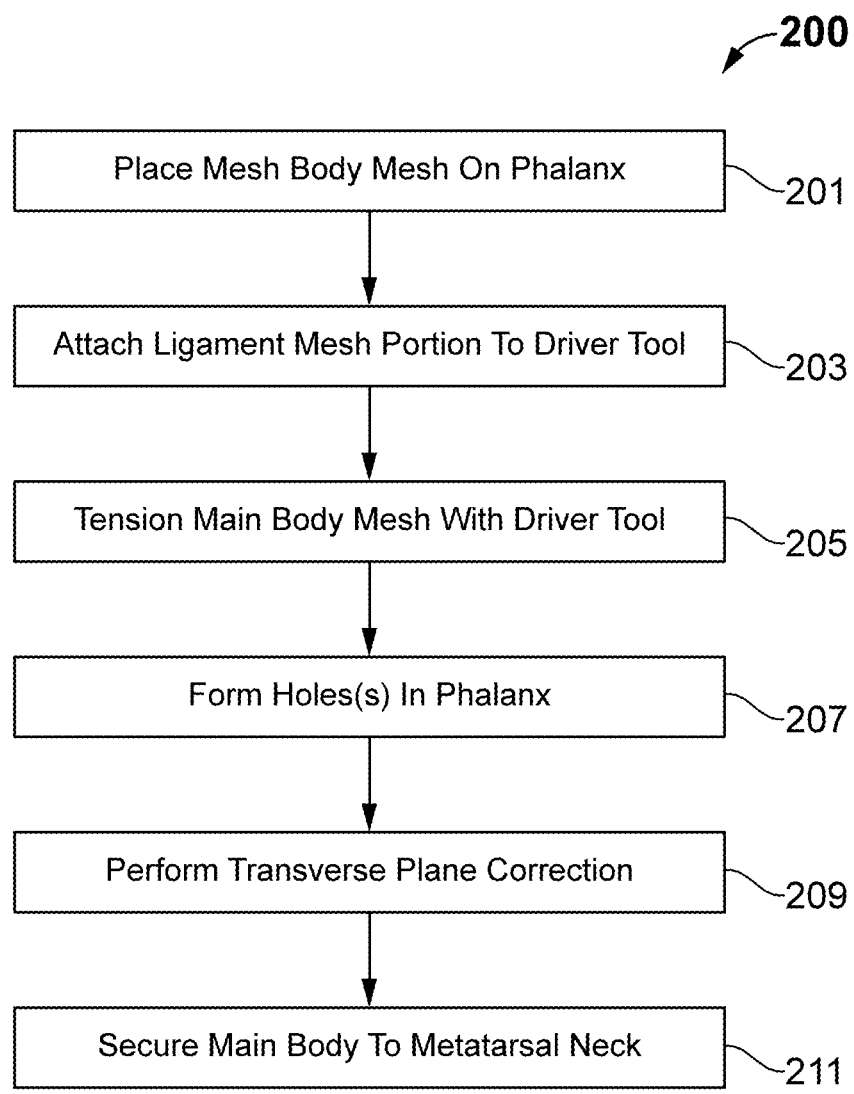
FIG. 13 illustrates a method of the present invention.

FIG. 13 illustrates a method 200 of the present invention. The soft tissue rebalancing device 100 is formed and the main body mesh portion 101 is positioned on the phalanx 111 in step 201. In step 203, the ligament mesh portion 105 is connected to the driver tool 113, and in step 205, the ligament mesh portion 205 is tightened to tension the main body mesh portion 101 by the driver tool 113. Holes are formed in the phalanx 111 in step 207. In step 209, traverse plane correction is performed in step 209, and in step 211, the mesh body portion 101 is secured to the metatarsal neck.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed.

The invention claimed is:

1. A soft tissue rebalancing method to rebalance a phalanx comprising the steps of:
   forming a mesh body portion having a ligament mesh portion and a braided mesh portion;
   positioning the mesh body portion on a phalanx;
   connecting the ligament mesh portion to a driver tool;
   tensioning the ligament mesh portion to increase the tension of the mesh body portion on the phalanx;
   performing transverse plane correction on the phalanx.

2. A soft tissue rebalancing method to rebalance a phalanx as in claim 1, wherein the method further comprising the step of securing the mesh body portion to a metatarsal neck.

3. A soft tissue rebalancing method to rebalance a phalanx as in claim 2, wherein the method further comprising the step of forming a hole in the phalanx.

4. A soft tissue rebalancing method to rebalance a phalanx as in claim 3, the ligament mesh portion is secured by a tack positioned in the hole.

\* \* \* \* \*